United States Patent [19]

Thies et al.

[11] Patent Number: 4,526,991
[45] Date of Patent: Jul. 2, 1985

[54] 2,6-DIOXA-BICYCLO-[2,2,2]-OCTANE-7-YL-ACETALDEHYDES

[75] Inventors: Peter W. Thies; Samuel David, both of Hanover, Fed. Rep. of Germany

[73] Assignee: Kali-Chemie Ag, Hanover, Fed. Rep. of Germany

[21] Appl. No.: 653,708

[22] Filed: Sep. 24, 1984

[30] Foreign Application Priority Data

Oct. 1, 1983 [DE] Fed. Rep. of Germany ....... 3335827

[51] Int. Cl.³ .......................................... C07D 319/14
[52] U.S. Cl. ................................................ 549/363
[58] Field of Search ........................... 549/363, 360

[56] References Cited

U.S. PATENT DOCUMENTS 3,917,651 11/1975 Thies .................................. 549/360

Primary Examiner—Ethel G. Love
Attorney, Agent, or Firm—Schwartz, Jeffery, Schwaab, Mack, Blumenthal & Evans

[57] ABSTRACT 2,6-Dioxa-bicyclo-[2,2,2]-octane-7-yl-acetaldehydes of the general Formula I,

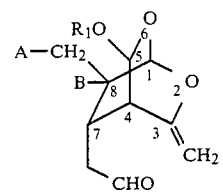

wherein $R_1$ is a benzyl or lower alkyl group, and A and B either are each hydrogen or together represent a single bond between their respective carbons, and a method for producing such compounds. The compounds are valuable intermediates in the synthesis of pharmacologically active substances having, for example, cardiovascular effects.

12 Claims, No Drawings

2,6-DIOXA-BICYCLO-[2,2,2]-OCTANE-7-YL-ACETALDEHYDES

BACKGROUND OF THE INVENTION

The present invention relates to new 2,6-dioxabicyclo-[2,2,2]-octane-7-yl-acetaldehydes and their preparation.

This novel type of compounds provides useful intermediates from which a novel group of pharmacologically active 2,10-dioxa-tricyclo-[5,3,1,0$^{3,8}$]-undecanes basically substituted in the 5-position can be prepared. For example, the new aldehyde compounds are intermediates in the synthesis of new N-(2,10-dioxa-tricyclo-[5,3,1,0$^{3,8}$]-undecane-5-yl)-tryptamine derivatives with valuable pharmacological properties, particularly cardiovascular effects such as blood pressure lowering effects.

SUMMARY OF THE INVENTION

It is therefore an object of the invention to provide new aldehyde intermediates from which new 2,10-dioxa-tricyclo-[5,3,1,0$^{3,8}$]-undecanes basically substituted in the 5-position can be prepared.

Specifically, it is an object to provide intermediates for preparing intermediates for preparing new N-(2,10-dioxa-tricyclo-[5,3,1,0$^{3,8}$]-undecane-5-yl)-tryptamine derivatives with valuable pharmacological properties, particularly cardiovascular effects, such as blood pressure lowering effects.

These and other objects of the invention are achieved by providing a compound corresponding to the formula:

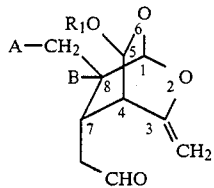

wherein $R_1$ represents a group selected from the group consisting of benzyl and lower alkyl groups and A and B each represent a hydrogen atom or A and B together represent a bond between the respective carbons.

Further objects, features and advantages of the present invention will become apparent from the following detailed description of preferred embodiments.

DETAILED DESCRIPTION OF PREFERRED EMBODIMENTS

The new compounds of the invention correspond to the general Formula I

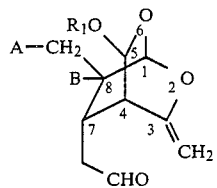

wherein $R_1$ represents either a benzyl or a lower alkyl group, and A and B either are each hydrogen or together represent a bond. Preferably, $R_1$ is a methyl group.

Substituents on carbon centers C5 and C8 in compounds of Formula I can be in either the R or S configuration. Formula I therefore represents several diasteromers. If A and B each represent hydrogen, C8 is preferably in the R configuration. C5 is preferably in the R configuration. The present invention comprises all diasteromers of compounds corresponding to the Formula I.

According to the invention, the compounds of Formula I are obtained by treating compounds corresponding to the general Formula II

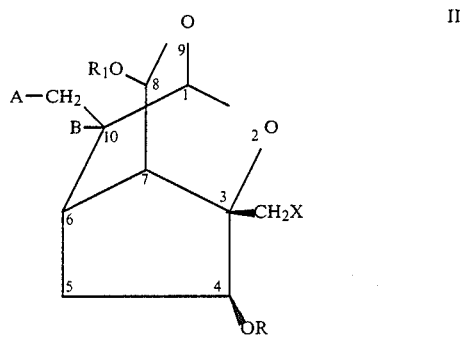

with a base in the presence of a solvent. In Formula II, $R_1$, A and B have the same meanings as above, X is either idodine or bromine, and R is either hydrogen or a lower acyl group. Preferably, compounds of Formula II are used where X is iodine and R is either hydrogen or an acetyl group.

Compounds of Formula II where R is hydrogen can be produced by hydrolyzing compounds of Formula II in which R is a acetyl group.

Suitable bases include alkali metal alkoxides such as sodium methoxide, alkali metal hydroxides and alkali metal carbonates such as potassium carbonate, or alkali metal hydrides such as sodium hydride. Furthermore, quarternary organic ammonium hydroxides, for example, quarternary lower alkyl ammonium hydroxides such as tetrabutyl ammonium hydroxide, or tertiary organic amines may also be used. Suitable tertiary organic amines specifically include tertiary lower alkyl amines such as triethylamine, tripropylamine and tributylamine, or cyclic tertiary amines such as 1,4-dimethylpiperazine, or pyridine.

As a practical matter, the reaction is desirably carried out in a solvent in which both the compounds of Formula II and the bases used are soluble. Examples of suitable solvents include: lower alcohols such as methanol and ethanol; open or cyclic ethers such as diethylether, tetrahydrofuran, or dioxane; or aromatic hydrocarbons such as toluene and benzene. If necessary, these solvents may be used mixed with water. If bases such as alkali metal alcoholates are reacted, corresponding lower alcohols are used as solvents. If hydroxides or carbonates are reacted, the solvents are preferably lower alcohols, optionally mixed with water. Cyclic ethers are the preferred solvents if alkali metal hydroxides are reacted.

The reaction can be carried out at temperatures between about 10° C. and 110° C., preferably between about room temperature and about 80° C. The length of the reaction may be between about 1 and 5 hours depending on the starting material and the reaction conditions. In case a compound of Formula II in which R is a lower acyl group is used, the kind of base, the amount of base, and the reaction conditions must, of course, be chosen appropriately for hydrolysis of the ester group.

Surprisingly, it is possible to cleave the carbon ring of compounds of Formula II under mild conditions according to the process of the invention. During the reaction, the configuration of all the asymmetric carbons is maintained so that the configuration of the substituents on carbons C5 and C8 in compounds of Formula I are the same as the corresponding configurations of the reacted starting material.

New compounds of Formula I, according to the invention, are useful as intermediates in the synthesis of new 2,10-dioxa-tricyclo-[5,3,1,0$^{3,8}$]-undecane derivatives basically substituted in the 5-position, which have valuable pharmacological properties.

Compounds of Formula I can, for instance, react with amines such as tryptamine of Formula III

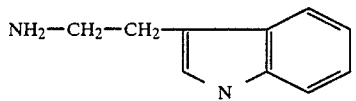

in a solvent R$_2$OH, where R$_2$ is a lower alkyl or alkanoyl group, to form a compound of the general Formula IV

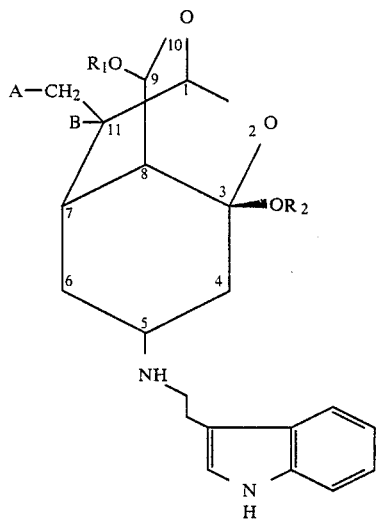

wherein R$_1$, R$_2$, A, and B all have meanings disclosed above. For example, Example 8, infra, illustrates reaction conditions under which compounds of Formula I can be converted to compounds of Formula IV by reaction with tryptamine in methanol. Compounds of the general Formula IV have valuable pharmacological properties, particularly cardiovascular effects such as, for instance, blood pressure lowering effects. Because of their blood pressure lowering effects, compounds of Formula IV are suited for use as antihypertensive drugs for treatment of high blood pressure. The cardiovascular effects of compounds of Formula IV can be demonstrated by standard pharmacological test methods on animals.

The effect of the substances on blood pressure, heartrate and EKG parameters during continuous i.v. infusion in anesthetized rats is determined by the method of Buschmann et al, *Journal of Cardiovascular Pharmacology*, Vol. 2, pp. 777–781 (1980). Male Wistar rats having a body weight of 330 to 370 grams are anesthetized with an i.p. application of 1.25 g/kg of urethane and tracheotomized. After an equilabration phase of 10 minutes, measurements are begun. Initial values are measured in a predrug phase of 5 minutes. Thereafter, the test substances are applied intravenously as a continuous infusion in isotonic sodium chloride solution, beginning with a dosage of 0.01 μmol/kg/min. The dosage is increased by a factor of 10 every 10 minutes without increase in the infusion volume. The mean blood pressure ($P_m$) is calculated from measurements of the systolic and diastolic blood pressures ($P_{syst}$ and $P_{diast}$). The following values are taken from the electrocardiagram (EKG): the atrioventricular conduction time (in milliseconds, corrected for changes in heart rate = $PR_c$); the time interval of intraventricular excitation (QRS); and the period of time from the beginning of the ventricular excitation to the maximum of the T-wave (R-αt). The heart rate is determined from the R—R interval.

From the measured blood pressure and heart rate parameters the respective ED$_{75}$ values in μmol/kg are calculated. This represents the total dosage which brings about a 25% reduction in a particular parameter with respect to the predrug value. From the EKG parameters the respective ED$_{125}$ values are calculated. The ED$_{125}$ is the total dosage in μmol/kg which increases the respective parameters by 25% of their predrug values. The minimum lethal dose (DL$_{min}$) in μmol/kg is also determined in the experiment.

In the aforedescribed experimental set-up, compounds of Formula IV exhibit blood pressure lowering effects in the dosage range from 1 to 100 μmol/kg. For example, the following values were determined for the compound 1R,3R,5S,7R,8R,9R-N-[3,9-dimethyoxy-11-methylene-(2,10-dioxa-tricyclo-[5,3,1,0$^{3,8}$]-undecane-5-yl]-tryptamine.

| Heart rate ED$_{75}$ | 41 μmol/kg |
| $P_{syst}$ ED$_{75}$ | 21 μmol/kg |
| $P_{diast}$ ED$_{75}$ | 5.9 μmol/kg |
| $P_m$ ED$_{75}$ | 9.7 μmol/kg |
| PR$_c$ED$_{125}$ | 93 μmol/kg |
| QRS ED$_{125}$ | 35 μmol/kg |
| R-αT ED$_{125}$ | 19 μmol/kg |
| DL$_{min}$ | 210 μmol/kg |

It is evident from these values that the compound has a highly specific blood pressure lowering effect, particularly on the diastolic blood pressure, and is highly tolerable.

The starting compounds of Formula II and their method of preparation are known, for example, from U.S. Pat. Nos. 4,158,061; 4,163,055; 4,182,889; 4,207,331; and 4,242,341, the disclosures of which are incorporated herein by reference and German Offenlegungsschrift No. 21 29 507. These starting materials can be synthesized by the processes described in these publications, or by methods analogous to the ones described therein. Compounds of Formula II, where A and B each represent a hydrogen, can be formed by hydrogenation of compounds of Formula II where A and B together represent a bond between their respective carbons. The hydrogenation reaction produces a mixture of epimers in which the R and S configurations are present in the ratio of 9:1. The epimers can be separated by fractional crystallization as described in U.S. Pat. No. 4,182,889.

The following illustrative examples are intended to further explain the synthesis of compounds of Formula I, but are not intended to limit the scope of the invention.

EXAMPLE 1

1R,4S,5R,7R-5-methoxy-3,8-dimethylene-2,6-dioxa-bicyclo-[2,2,2]-octane-7-yl-acetaldehyde.

A solution of 7.6 g of 1R,3S,4S,6R,7S,8R-3-iodomethyl-4-acetoxy-8-methyoxy-10-methylene-2,9-dioxa-tricyclo-[4,3,1,0$^{3,7}$]-decane in 100 ml of absolute methanol is added to a sodium methylate solution made by dissolving 0.44 g of sodium in 40 ml of absolute methanol. The mixture is allowed to react at 60° C. for 4.5 hours and then is worked up as follows: it is poured onto ice water, thoroughly salted out with sodium chloride, and extracted with ether. Subsequently, a few drops of glacial acetic acid are added to the ether phase; it is dried over sodium sulfate, filtered, and concentrated by removal of solvent. The residue is 4.29 g of crude 1R,4S,5R,74-5-methoxy-3,8-dimethylene-2,6-dioxa-bicyclo-[2,2,2]-octane-7-yl-acetaldehyde.

The crude product can be used directly in this form as an intermediate in the further conversion into a compound of Formula IV. The crude product can be chromatographically purified over silica gel, with n-hexane/ether as eluent. After concentration from the eluent, the product, which is pure according to thin layer chromatographic analysis, is crystallized from n-hexane/ether. 1R,4S,5R,7R-5-methoxy-3,8-dimethylene-2,6-dioxa-bicyclo-[2,2,2]-octane-7-yl-acetaldehyde has a melting point 56° to 59° C. The IR-spectrum shows peaks at 3070 cm$^{-1}$, 1725 cm$^{-1}$, 1675 cm$^{-1}$, 1170 cm$^{-1}$, 1075 cm$^{-1}$, 960 cm$^{-1}$.

EXAMPLE 2

1R,4S,5R,7R-5-methoxy-3,8-dimethylene-2,6-dioxa-bicyclo-[2,2,2]-octane-7-yl-acetaldehyde Six grams of 1R,3S,4S,6R,7S,8R-3-iodomethyl-4-acetoxy-8-methoxy-10-methylene-2,9-dioxa-tricyclo-[4,3,1,0$^{3,7}$]-decane are added to a sodium methylate solution made by dissolving 2.5 g of sodium in 250 ml of absolute methanol. The reaction mixture is stirred at a bath temperature of 60° C. for 1.5 hours under nitrogen and then is worked up as follows. The volume of the solution is reduced to one quarter of its original volume by rotary evaporation. To the concentrated solution is added 100 g of saturated ammonium sulfate solution, whereby NH$_3$ is evolved. Thereafter, the resulting solution is extracted 5 times with a total volume of 500 ml of ether. The ether extracts are washed with 50 ml of sodium sulfate solution and subsequently with water; dried over magnesium sulfate, and evaporated. 2.9 g of crude 1R,4S,5R,7R-5-methoxy-3,8-dimethylene-2,6-dioxa-bicyclo-[2,2,2]-octane-7-yl-acetaldehyde are obtained.

This crude product can be used, without further purification, in the synthesis of compounds of Formula IV. If desired, it can be further purified as described in Example 1. The purified product is identical to that obtained in Example 1.

EXAMPLE 3

1R,4S,5R,7R,8R-5-methoxy-8-methyl-3-methylene-2,6-dioxabicyclo-[2,2,2]-octane-7-yl-acetaldehyde A. A solution of 10 g of 1R,3S,4S,6R,7S,8R,10R-3-iodomethyl-4-acetoxy-8-methoxy-10-methyl-2,9-dioxa-tricyclo-[4,3,1,0$^{3,7}$]-decane in 220 ml of methanol is mixed with 3.6 g of potassium carbonate, and the resulting reaction mixture is stirred at room temperature for approximately 1 hour and then is worked up as follows. It is diluted with water and extracted with methylene chloride. The organic phase is separated, dried over sodium sulfate, filtered and the solvent removed under vacuum. 8.7 g of 1R,3S,4S,6R,7S,8R,10R-3-iodomethyl-4-acetoxy-8-methoxy-10-methyl-2,9-dioxa-tricyclo-[4,3,1,0$^{3,7}$]-decane, with a melting point of 92° to 93° C., are obtained.

B. A solution of 3.24 g of 1R,3S,4S,6R,7S,8R,10R-3-iodomethyl-4-hydroxy-8-methoxy-10-methyl-2,9-dioxa-tricyclo-[4,3,1,0$^{3,7}$]-decane in 50 ml absolute methanol is mixed with a sodium methylene solution formed by dissolving 0.23 g sodium in 50 ml absolute methanol. The reaction mixture is stirred for about 3 hours at a temperature of 60° C. Thereafter, the reaction mixture is worked up by pouring it into ice water, salting out well with sodium chloride, and extracting with ether. The ether phase is mixed with a few drops of glacial acetic acid, dried over sodium sulfate, filtered, and the solvent removed to dryness under reduced pressure. The residue is 2.7 g of crude 1R,4S,5R,7R,8R-5-methoxy-8-methyl-3-methylene-2,6-dioxabicyclo-[2,2,2]-octane-7-yl-acetaldehyde.

This crude product can be used, without further purification, as an intermediate in the synthesis of the compounds of Formula IV. The crude product can be purified by silica gel chromatography, using n-hexane with up to 15% ether as eluent. After removal of the eluent, the product which is pure according to thin layer chromatographic analysis is obtained as an oil. I.R.-spectrum: 1725 cm$^{-1}$, 1675 cm$^{-1}$, 1060 cm$^{-1}$.

EXAMPLE 4

1R,4S,5R,7R,8R-5-methoxy-8-methyl-3-methylene-2,6-dioxabicyclo-[2,2,2]-octane-7-yl-acetaldehyde One gram of 1R,3S,4S,6R,7S,8R,10R-3-iodomethyl-4-acetoxy-8-methoxy-10-methyl-2,9-dioxa-tricyclo-[4,3,1,0$^{3,7}$]-decane in 10 ml of methanol is mixed with 0.35 g potassium carbonate. The reaction mixture is stirred for 5 hours at 60° C. Thereafter, the reaction mixture is worked up as follows. It is diluted with water and extracted with methylene chloride. The organic phase is dried over sodium sulfate, filtered, and the solvent removed to dryness under reduced pressure. 0.46 g of crude 1R,4S,5R,7R,8R-5-methoxy-8-methyl-3-methylene-2,6-dioxa-bicyclo-[2,2,2]-octane-7-yl-acetaldehyde are obtained.

This product can be used directly as an intermediate in the synthesis of compounds of Formula IV. If desired, the crude product can be purified as described in Example 3. The purified product is identical to that obtained in Example 3.

EXAMPLE 5

1R,4S,5R,7R,8R-5-methoxy-8-methyl-3-methylene-2,6-dioxa-bicyclo-[2,2,2]-octane-7-yl-acetaldehyde A solution of 1 gram of 1R,3S,4S,6R,7S,8R,10R-3-iodomethyl-4-hydroxy-8-methoxy-10-methyl-2,9-dioxa-tricyclo-[4,3,1,0³,⁷]-decane in 10 ml of absolute tetrahydrofuran is added dropwise into 0.14 g of sodiumhydride (50% solution in oil) in 10 ml absolute tetrahydrofuran. The reaction mixture is stirred for 3 hours at room temperature and then is worked up. Ice water is added, carefully mixed, and thereafter the mixture is extracted with methylene chloride. The organic phase is dried over sodium sulfate, filtered, and the solvent removed to dryness under reduced pressure. 0.68 g of crude 1R,4S,5R,7R,8R-5-methoxy-8-methyl-3-methylene-2,6-dioxa-bicyclo-[2,2,2]-octane-7-yl-acetaldehyde are obtained.

This product can be used directly as an intermediate in the synthesis of compounds of Formula IV. If desired, the crude product can be purified as described in Example 3. The purified product is identical to that obtained in Example 3.

EXAMPLE 6

1R,4S,5R,7R-5-isobutoxy-3,8-dimethylene-2,6-dioxa-bicyclo-[2,2,2]-octane-7-yl-acetaldehyde Four and one-half grams of 1R,3S,4S,6R,7S,8R-3-iodomethyl-4-acetoxy-8-isobutoxy-10-methylene-2,9-dioxa-tricyclo-[4,3,1,0³,⁷]-decane, with a melting point of between 45° and 50° C., are reacted as described in Example 1 with a sodium methylate solution prepared by dissolving 1.25 g of sodium in 200 ml of methanol. The 1R,3S,4S,6R,7S,8R-3-iodomethyl-4-acetoxy-8-isobutoxy-10-methylene-2,9-dioxa-tricyclo-[4,3,1,0³,⁷]-decane is produced in a known manner by reacting didrovaltratum with isobutanol and hydroiodic acid. After working up the reaction mixture, 3.5 g of crude 1R,4S,5R-5-isobutoxy-3,8-dimethyene-2,6-dioxa-bicyclo-[2,2,2]-octane-7-yl-acetaldehyde are obtained as an oil. I.R. spectrum: 3070 cm⁻¹, 1725 cm⁻¹, 1675 cm⁻¹, 1175 cm⁻¹, 1075 cm⁻¹, 960 cm⁻¹. This product can be directly used as an intermediate in the synthesis of compounds of Formula IV.

EXAMPLE 7

1R,4S,5R,7R-5-benzyloxy-3,8-dimethylene-2,6-dioxa-bicyclo-[2,2,2]-octane-7-yl-acetaldehyde Four and two-tenths grams of 1R,3S,4S,6R,7S,8R-3-iodomethyl-4-acetoxy-8-benzyloxy-10-methylene-2,9-dioxa-tricyclo-[4,3,1,0³,⁷]-decane, having a melting point of 69°-70° C. and produced in a known manner by reacting didrovaltratum with benzyl alcohol and hydroiodic acid, are reacted with a sodium methylate solution prepared by dissolving 1.2 g of sodium in 200 ml of methanol, as described in Example 1. After working up this reaction mixture, 3.2 g of crude 1R,4S,5R,7R-5-benzyloxy-3,8-dimethylene-2,6-dioxa-bicyclo-[2,2,2]-octane-7-yl-acetaldehyde are obtained as an oil. I.R.-spectrum: 3065 cm⁻¹, 3030 cm⁻¹, 1725 cm⁻¹, 1675 cm⁻¹, 1495 cm⁻¹, 1070 cm⁻¹, 960 cm⁻¹.

This product can be directly used as an intermediate in the synthesis of compounds of Formula IV.

EXAMPLE 8

Further reaction of 1R,4S,5R,7R-5-methoxy-3,8-dimethylene-2,6-dioxa-bicyclo-[2,2,2]-octane-7-yl-acetaldehyde to produce 1R,3R,5S,7R,8R,9R- and 1R,3R,5R,7R,8R,9R-N-(3,9-dimethoxy-11-methylene-2,10-dioxa-tricyclo-[5,3,1,0³,⁸]-undecane-5-yl)-tryptamine.

The 1R,4S,5R,7R-5-methoxy-3,8-dimethylene-2,6-dioxa-bicyclo-[2,2,2]-octane-7-yl-actealdehyde yield obtained from 4 g of 1R,3S,4S,6R,7R,8R-3-iodomethyl-4-acteoxy-8-methoxy-10-methylene-2,9-dioxa-tricyclo-[4,3,1,0³,⁷]-decane, according to the procedure of Example 2, is dissolved in 100 ml of absolute methanol. The resulting solution is mixed under nitrogen with 2 g tryptamine hydrochloride, and the reaction mixture is stirred at a bath temperature of 60° C. for 3.5 hours. Thereafter, the reaction mixture is worked up by distilling off the methanol, alkalizing the remaining reaction mixture with concentrated sodium carbonate, and extracting with methylene chloride. The organic phase is dried over magnesium sulfate, and the solvent is removed. The yield is 4 g of a red-colored crude product. The crude product is purified by column chromatography under pressure, using chloroform with 5% methanol as the elution solvent. The eluate yields 890 mg of non-polar 1R,3R,5S,7S,8R,9R-N-(3,9-dimethoxy-11-methylene-2,10-dioxa-tricyclo-[5,3,1,0³,⁸]-undecane-5-yl)-tryptamine as a colorless solid foam.

$[\alpha]_D^{20} = 3.3°$.

molecular weight: calculated = 384.2049, found = 384.2048.

Mass spectrum (130° C.): M⁺ = 384(4), 383(11), 352(11), 253(43), 221(21), 192(27), 179(42), 175(9), 144(11), 131(100).

In addition, a polar byproduct, crude 1R,3R,5R,7R,8R,9R-N-(3,9-dimethoxy-11-methylene-2,10-dioxa-tricyclo-[5,3,1,0³,⁸]-undecane-5-yl)-tryptamine, is also obtained from the eluate. Following additional purification by preparative thin layer chromatography, using chloroform with 5% methanol as the elution solvent, 125 mg of the pure product are obtained as a colorless solid foam.

molecular weight: calculated = 384.2049, found = 384.2048.

Mass spectrum (110° C.): M⁺ = 384(7), 353(8), 254(100), 242(12).

The foregoing description has been set forth merely to illustrate the invention and is not intended to be limiting. Since modifications of the described embodiments incorporating the spirit and substance of the invention may occur to persons skilled in the art, the scope of the invention is to be limited solely with respect to the appended claims and equivalents.

What is claimed is:

1. A compound corresponding to the formula:

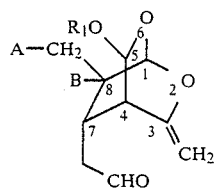

wherein $R_1$ represents a group selected from the group consisting of benzyl and lower alkyl groups and A and B each represent a hydrogen atom or A and B together represent a bond between their respective carbons.

2. A compound according to claim 1 wherein A and B each represent a hydrogen atom.

3. A compound according to claim 1 wherein A and B together represent a bond between their respective carbons.

4. A compound according to claim 1 wherein $R_1$ represents a methyl group.

5. A compound according to claim 1 wherein $R_1$ represents a benzyl group.

6. A compound according to claim 1 wherein $R_1$ represents an isobutyl group.

7. A method for producing a compound corresponding to the formula:

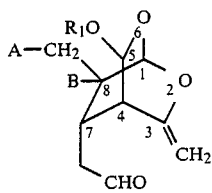

I wherein $R_1$ represents a group selected from the group consisting of benzyl and lower alkyl groups and A and B each represent a hydrogen atom or A and B together represent a bond between their respective carbons comprising reacting a compound corresponding to the formula:

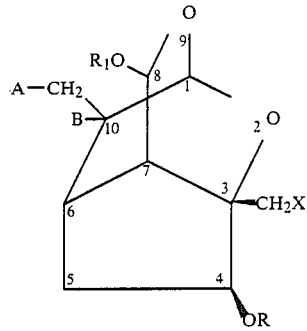

II wherein $R_1$, A and B have the meanings defined above, X represents a halogen atom selected from the group consisting of bromine and iodine, and R represents a hydrogen atom or a lower acyl group, with a base in the presence of a solvent.

8. A method according to claim 7 further comprising the step of isolating the resulting product.

9. A method according to claim 7 wherein X represents an iodine atom.

10. A method according to claim 7 wherein R represents an acetyl group.

11. A method according to claim 7 wherein said base is selected from the group consisting of alkali metal alkoxides, alkali metal hydroxides, alkali metal carbonates, alkali metal hydrides, quaternary ammomium hydroxides, and tertiary amines.

12. A method according to claim 7 wherein said solvent is selected from the group consisting of lower alcohols, ethers and aromatic hydrocarbons.

* * * * *